(12) United States Patent
Schleep et al.

(10) Patent No.: US 7,723,543 B2
(45) Date of Patent: *May 25, 2010

(54) METHOD FOR THE CONTINUOUS PRODUCTION OF ALKYL AMINO ACRYL AMIDES

(75) Inventors: Volker Schleep, Einhausen (DE); Thomas Mertz, Bensheim (DE)

(73) Assignee: Evonik Roehm GmbH, Darmstadt (DE)

( * ) Notice: Subject to any disclaimer, the term of this patent is extended or adjusted under 35 U.S.C. 154(b) by 271 days.

This patent is subject to a terminal disclaimer.

(21) Appl. No.: 11/719,564

(22) PCT Filed: Nov. 18, 2005

(86) PCT No.: PCT/EP2005/012362

§ 371 (c)(1),
(2), (4) Date: May 17, 2007

(87) PCT Pub. No.: WO2006/056366

PCT Pub. Date: Jun. 1, 2006

(65) Prior Publication Data

US 2009/0149674 A1    Jun. 11, 2009

(30) Foreign Application Priority Data

Nov. 23, 2004    (DE) .................. 10 2004 056 629

(51) Int. Cl.
*C07C 231/00*    (2006.01)

(52) U.S. Cl. .................. 564/134; 564/135; 564/137; 564/138; 564/141

(58) Field of Classification Search .................. 564/134, 564/135, 137, 138, 141
See application file for complete search history.

(56) References Cited

U.S. PATENT DOCUMENTS

| 4,675,442 A * | 6/1987 | Besecke et al. ............. 564/135 |
| 2007/0149811 A1 | 6/2007 | Schleep et al. |
| 2008/0194862 A1 | 8/2008 | Ackermann et al. |
| 2008/0194875 A1 | 8/2008 | Ackermann et al. |

FOREIGN PATENT DOCUMENTS

| DE | 40 27 843 | 3/1992 |
| DE | 103 23 699 | 12/2004 |
| GB | 2248234 | * 4/1992 |

OTHER PUBLICATIONS

U.S. Appl. No. 12/296,780, filed Oct. 10, 2008, Schleep, et al.
U.S. Appl. No. 12/307,773, filed Jan. 7, 2009, Ackermann, et al.
U.S. Appl. No. 12/517,199, filed Jun. 2, 2009, Gropp et al.
U.S. Appl. No. 12/422,123, filed Mar. 20, 2009, Gropp et al.
U.S. Appl. No. 12/516,629, filed May 28, 2009, Gropp et al.
U.S. Appl. No. 12/517,366, filed Jun. 3, 2009, Gropp et al.
U.S. Appl. No. 12/515,545, filed May 20, 2009, Gropp et al.
U.S. Appl. No. 12/515,964, filed May 22, 2009, Gropp et al.
U.S. Appl. No. 12/517,673, filed Jun. 4, 2009, Gropp et al.

* cited by examiner

*Primary Examiner*—Taylor Victor Oh
(74) *Attorney, Agent, or Firm*—Oblon, Spivak, McClelland, Maier & Neustadt, L.L.P.

(57) ABSTRACT

The invention relates to a method for the continuous production of alkyl amino acryl amides by reacting alkyl acrylates with high-boiling amines. A specific preparation technique is used in order to achieve hitherto unobtainable product qualities. Very high spatial, temporal and overall yields can also be obtained.

20 Claims, 1 Drawing Sheet

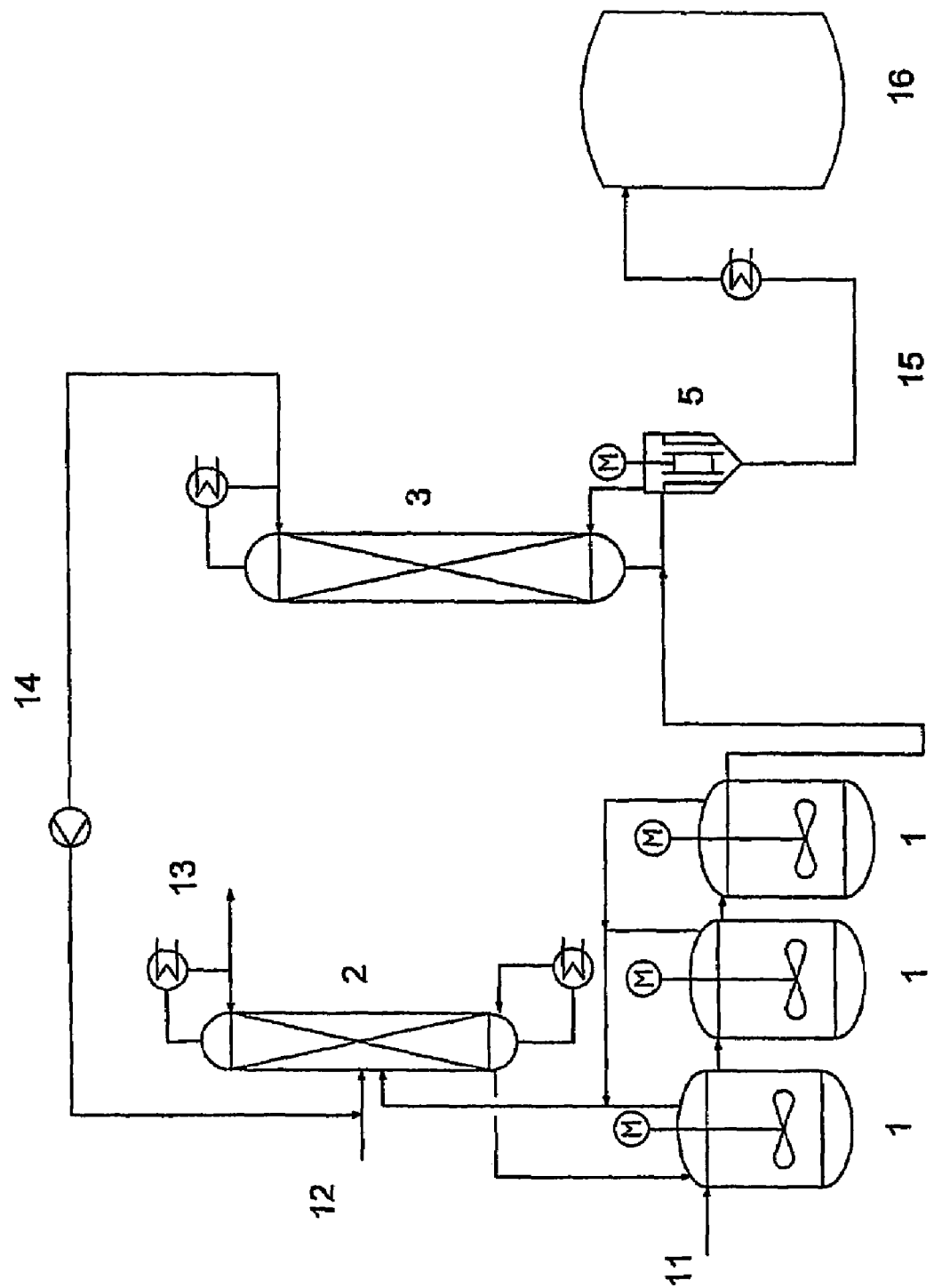

METHOD FOR THE CONTINUOUS PRODUCTION OF ALKYL AMINO ACRYL AMIDES

FIELD OF THE INVENTION

The invention relates to a continuous process for preparing alkylaminoacrylamides (C) by continuous aminolysis of, for example, butyl acrylate (A where $R_1=C_4$) with amines (B) to release butanol (D where $R_1=C_4$) according to the following reaction equation:

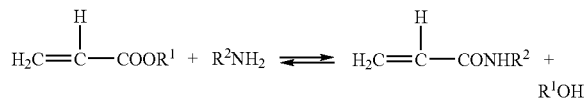

where $R^1$ = linear or branched alkyl radical having 3 to 10 carbon atoms $R^2$ is a linear, branched or cyclic alkyl radical, an aryl radical which may also be substituted by one or more alkyl groups, the linear, cyclic or branched alkyl radical may have a length of 1-12 carbon atoms, for example methyl, ethyl, propyl, isopropyl, butyl, isobutyl, tert-butyl, pentyl, hexyl, heptyl, octyl, isooctyl, nonyl, decyl, undecyl, and may optionally be mono- or polysubstituted by $NR^3R^4$ or $OR^5$, either $R^3$ or $R^4$ may assume the definition of hydrogen and also:

$R^3$, $R^4$ or $R^5$ may either be the same or different and be an alkyl group having 1-12 carbon atoms, for example methyl, ethyl, propyl, isopropyl, butyl, isobutyl, tert-butyl, pentyl, hexyl, heptyl, octyl, iso-octyl, nonyl, decyl, undecyl or hydrogen.

$R^2$ may also be

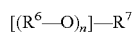

where $R^6$ may be a $C_1$-$C_4$-alkyl group which may also be branched, for example methyl, ethyl, propyl, isopropyl, butyl, isobutyl or tert-butyl.

Alkylamido (meth)acrylates m: 1-4

$R^7$ may be the methyl group or the ethyl group.

Useful amines are, for example, the following compounds; dimethylaminoethylamine, diethylaminoethylamine, dipropylaminoethylamine, diisopropylaminoethylamine, dibutylaminoethylamine, diisobutylaminoethylamine, dimethylaminopropylamine, diethylaminopropylamine, dipropylaminopropylamine, diisopropylaminopropylamine, dibutylaminopropylamine, diisobutylaminopropylamine, dimethylaminobutylamine, diethylaminobutylamine, dipropylaminobutylamine, diisopropylaminobutylamine, dibutylaminobutylamine, diisobutylaminobutylamine, methylamine, eyelohexylamine, dimethylaminohexylamine, diethylaminohexylamine.

In addition to dimethylaminopropylamine, particular preference is given to dimethylaminoethylamine, dimethylaminobutylamine, dimethylaminopentylamine and dimethylaminohexylamine.

STATE OF THE ART

The literature describes many batchwise transesterification processes in conjunction with different catalysts.

The search for more economically viable processes led to the discovery of continuous transesterification processes in which the reactants are fed continuously and the products are removed continuously. The continuous transesterification processes have the following advantages over the batchwise transesterification processes: the process can be automated more readily and can be operated with reduced personnel requirements, the product quality is better reproducible and less variable, the plant capacity increases owing to the absence of the sequential execution of the individual preparation steps (charging, reaction, low boiler removal, product removal, emptying). The process has a higher space-time yield than a batch process.

Continuous transesterification processes are known, EP 0 960 877 (Elf Atochem S.A.) describes a continuous process for preparing methacrylate esters of dialkylamino alcohols, Dialkylamino alcohols are reacted with generally methyl (meth)acrylate and the dialkylaminoalkyl (meth)acrylate is obtained by the following process:

The mixture of the starting materials (methyl (meth)acrylate and dialkylamino alcohol) is fed continuously together with a tetraalkyltitanate catalyst (for example tetrabutyl, tetraethyl or tetra(2-ethylhexyl) titanate) and at least one polymerization inhibitor (for example phenothiazine, tert-butylcatechol, hydroquinone monomethyl ether or hydroquinone) to a stirred reactor where the conversion to the dialkylamino (meth)acrylate with simultaneous continuous removal of the azeotropic methyl (meth)acrylate/methanol mixture is effected at a temperature of 90-120° C. The crude reaction mixture (crude ester) is fed to a first distillation column in which, under reduced pressure, a substantially catalyst-free stream is drawn off at the top of the distillation column, and the catalyst and also a little dialkylaminoalkyl (meth)acrylate are drawn off in the bottom of the distillation column. The top stream of the first distillation column is then fed to a second distillation column in which, under reduced pressure, a stream of low-boiling products comprising a little dialkylaminoalkyl (meth)acrylate is drawn off at the top, and a stream consisting of mainly dialkylaminoalkyl (meth)acrylate and also polymerization inhibitor (s) is drawn off at the bottom and is fed to a third distillation column. In the third distillation column, a rectification is carried out under reduced pressure, in which the desired pure dialkylaminoalkyl (meth)acrylate ester is drawn off at the top, and substantially the polymerization inhibitor or the polymerization inhibitors at the bottom. The bottom stream of the first distillation column, after further purification with the aid of a film evaporator, is recycled into the reactor, just like the top stream from the second distillation column.

This process dispenses with dewatering of the alcohols before use, which can lead to intensified deactivation of the tetraalkyl titanate used owing to hydrolysis up to and including the formation of undesired solid precipitates. Furthermore; the process has the disadvantage that the catalyst is thermally stressed at relatively high temperatures in the bottom of the first distillation column. This can lead very easily to the decomposition of the catalyst.

In this process, both the unconverted reactants and the product are rectified overhead twice in total. This entails very high energy costs and a total of 4 rectification columns, some of which have to have very large dimensions. The process is therefore burdened with very high capital and operating costs.

EP 0 968 995 (Mitsubishi Gas Chemical Comp.) describes a continuous process for preparing alkyl (meth)acrylates using a reaction column. In this process, the transesterification reaction is effected directly in a distillation column (i.e. reactor and distillation column for removing the methyl (meth)acrylate/methanol azeotrope form one apparatus) to which the starting materials (methyl (meth)acrylate and alcohol) are fed continuously. The catalyst needed, here likewise preferably a titanium compound, is disposed in the distillation column. In the case of a homogeneous catalyst, the catalyst is metered continuously into the distillation column. However, the use of homogeneous catalysts in a distillation column leads, owing to a flushing effect, as a result of the liquid reflux, to increased catalyst demand in the distillation column and, in the event of occurrence of a solid catalyst precipitate, to fouling of the column internals. In the case of a heterogeneous catalyst, the catalyst is disposed in the reaction column. However, the positioning of the catalyst in the distillation column is disadvantageous because an increased pressure drop then occurs in the distillation column and a very high level of cost and inconvenience additionally has to be accepted for the regular cleaning of the distillation column. Furthermore, heterogeneous catalysts can deactivate, for example, owing to undesired polymerization.

DE 4 027 843 (Röhm GmbH) describes a continuous process for preparing N-substituted (meth)acrylamides by aminolysis of alkyl esters of (meth)acrylic acid with aliphatic and aromatic amines. The reaction temperature is >150°; the pressure is approx. 160 bar. No catalyst is employed.

OBJECT

It is an object of the present invention to provide a continuous process for the aminolysis of acrylic esters which avoids the disadvantages of the two above-described processes. Furthermore, the novel process shall provide a product which is better in quality than those present on the market to date. A better quality is understood to mean a lower crosslinker content or a lower content of addition products of the amines to the double bond of the starting ester or to the double bond of the product amide.

In addition, it shall be possible by the novel process to prepare amino acrylates with a very low level of complexity and in an energetically more favourable (i.e. less expensive) manner. The personnel demands for operating the plant shall be reduced.

This object, and also other objects which are not specifically detailed but can be immediately discerned or derived from the introductory discussion of the prior art, are achieved by a process having the features of Claim 1. Advantageous modifications of the process according to the invention are protected in the claims dependent upon Claim 1.

PROCESS DESCRIPTION

The process is illustrated schematically in FIG. 1.

EXPLANATIONS OF THE REFERENCE NUMERALS, FIG. 1

1. Reaction apparatus
2. Low boiler discharge distillation column
3. Low boiler distillation column
5. Film evaporator
11. Acrylate feed and catalyst feed
12. Amine feed
13. Low boiler discharge
14. Low boiler circulation stream
15. Crude product
16. Reservoir vessel for further distillation steps The acrylate feed reactant (11) is fed continuously to a suitable reaction apparatus (1), for which either a single reaction vessel or a battery of a plurality of reaction vessels connected in series can be used. Such a battery can consist, for example, of 2, 3, 4, 5, 6 or, if appropriate, more individual reaction vessels. In a preferred embodiment, a battery composed of 3 continuous stirred tanks arranged in series is used.

The acrylate feed reactant (11) can be effected in various ways. It is possible, for example, to feed the reactant stream (11) only to the first reaction vessel of the battery or else to divide the reactant stream (11) into substreams and to feed these substreams to all or only to some of the series-connected reaction vessels of the battery. It is equally possible to undertake the feeding of the reactant stream (11) via the apparatus (2) and/or the reaction apparatuses (1). It may be advantageous to feed the reactant stream (11) only into the apparatus (2) or, in a further embodiment, to divide the reactant stream (11) into sub-streams which are then fed either to the apparatus (2) or to the first or, if appropriate, a plurality of the reaction vessels of the battery.

It is sensible that all reaction vessels have a vapour draw to the distillation column (2) for removing the alcohol released in the reaction.

The flow management to the reactors and out of them does not necessarily have to be as shown in the flow diagram. In particular embodiments, it has been found to be advantageous to introduce the discharge of one tank of the battery from the bottom into the next tank of the battery in each case.

The amine (12) is fed continuously to the distillation column (2) for dewatering.

The tetraalkoxytitanate required as a catalyst (the tetraalkoxytitanate content in relation to acrylic ester A used is preferably 0.2-4% by weight) is metered, like the polymerization inhibitor(s), likewise preferably continuously into the reaction apparatus (1). However, the aminolysis catalysts used may also be all transesterification catalysts known from the prior art. Useful catalysts are, for example, zirconium acetylacetonate and further 1,3-diketonates of zirconium; it is also possible to use mixtures of alkali metal cyanates or alkali metal thiocyanates and alkali metal halides, and also tin compounds, for example dioctyltin oxide, alkaline earth metal oxides or alkaline earth metal hydroxides, for example CaO, $Ca(OH)_2$, MgO, $Mg(OH)_2$ or mixtures of the aforementioned compounds, and also alkali metal hydroxides, alkali metal alkoxides and lithium chloride and lithium hydroxide; it is also possible to use mixtures of the aforementioned compounds with the aforementioned alkaline earth metal compounds and the Li salts, dialkyltin oxides, for example dioctyltin oxide, alkali metal carbonates, alkali metal carbonates together with quaternary ammonium salts, for example tetrabutylammonium hydroxide or hexadecyltrimethylammonium bromide, and also mixed catalysts composed of diorganyltin oxide and organyltin halide, acidic ion exchangers, phosphorus-molybdenum heteropolyacids, titanium alkoxides, for example isopropyl titanate, chelate compounds of the metals titanium, zirconium, iron or zinc with 1,3-dicarbonyl compounds, lead compounds, for example lead oxides, lead hydroxides, lead alkoxides, lead carbonates or lead salts of carboxylic acids. Particular preference is given to a catalyst mixture composed of dialkyltin oxide and alkyl titanate, for example dioctyltin oxide and isopropyl titanate in a ratio of approx. 2.5:1 (% by weight/% by weight).

The catalyst or the catalyst mixture is used in amounts of 0.1-10% by weight, preferably 0.2-7% by weight, based in each case on the acrylate used.

Suitable alkyl acrylates are all acrylates having a linear or branched alkyl radical having 3 to 10, preferably 3 to 6 and more preferably 3 or 4 carbon atoms. Typical examples thereof are propyl acrylate, isopropyl acrylate, n-butyl acrylate, isobutyl acrylate, 3-methylbutyl acrylate, amyl acrylate, neopentyl acrylate, hexyl acrylate, cyclohexyl acrylate, heptyl acrylate, n-octyl acrylate, ethylhexyl acrylate or decyl acrylate.

The amines used may be all compounds $R^2NH_2$ whose $R^2$ radical consists of 1-12, preferably 2-8 or more preferably of 2-4 carbon atoms. Examples of typical structures and specific compounds are listed at the start of this application.

It is still clear to those skilled in the art in the field that the starting materials are selected particularly advantageously in such a way that the equilibrium can be shifted to the side of the products with the removal of the alcohol from the reaction mixture. The alcohol can be removed distillatively by virtue of its lower boiling point in comparison to the amine used and/or by the formation of an azeotrope.

Useful polymerization inhibitors are, for example, hydroquinone, 4-hydroxy-2,2,6,6-tetramethylpiperidinooxyl or else bis(2-methoxycarbonylpropyl) sulphide or hydroquinone monomethyl ether in conjunction with oxygen.

The amine used may comprise water. The amount of water in the amine used is between 50 and 500 ppm (0.05-0.005% by weight) in the case of amine. Before entry into the reaction apparatus; the amine is preferably dewatered distillatively by means of the distillation column (2). This removes the water present in the amine overhead. To prevent contamination of the low boiler discharge (13) with the amine used, the amine is preferably introduced in the lower section of the distillation column (2). The amine used may also be dewatered in other ways:
- by an upstream dewatering distillation column or
- by treating with a dewatering agent, for example a molecular sieve,
- or
- by a membrane separation process, for example a pervaporation.

The dewatering is important since the water present in the amine can lead to irreversible damage of the catalyst (for example tetraalkyl titanate) in the reactor. The water present in the amine leads to the formation of by-products and is therefore to be strictly avoided. This dewatering step prevents the hydrolysis of the catalyst and the associated costs as a result of increased catalyst use amounts and as a result of problems with solid precipitates. Moreover, the purity of the product is increased by a reduced fraction of by-products.

The reaction is effected in the reaction apparatus (1) at a temperature in the range between 80 and 180° C. depending on the substance system and operating pressure. The temperature range is preferably between 110 and 160° C. To increase the reaction rate, the alcohol released in the reaction is drawn off (13) by means of the distillation column (2) from the reaction mixture, optionally also as an azeotrope with the alcohol. This can be effected at atmospheric pressure, at elevated pressure or at reduced pressure. The reaction mixture, which consists for the most part of the product alkyl acrylate amide, unconverted acrylate and amine, and also small amounts of alcohol, of the catalyst, of the polymerization inhibitors and of a fraction of by-products, is fed after approx. 0.5-3 hours of the reactor residence time (preference is given to a residence time of 1-2 hours) to a continuous falling-film evaporator (5). The vapours of the falling-film evaporator (5) are fed to a low boiler distillation column (3). There, the low-boiling components in relation to the product amide, predominantly product alcohol and unconverted reactant acrylate and amine, are removed under reduced pressure, preferably in the range of approx. 1-500 mbar. These are drawn off via the top of the distillation column (3) and recycled (14) into the reactor region or into the distillation column (2). As a result of this circulation stream, a high conversion based on the reactants and the overall process is achieved.

The crude amide (15) which is obtained in the effluent of the falling-film evaporator (5) and is still contaminated with catalyst, polymerization inhibitor and high-boiling by-products contains preferably >80% by weight of product amide and is fed for workup to a further vacuum distillation stage which works in the preferred pressure range between 0.1 and 200 mbar. Here, the highly pure product amide is removed distillatively as the top product.

The by-products formed in the process constitute high-boiling components in relation to the reactant amine and the reactant acrylate, and thus pass as an impurity into the product amide, as a result of which the product quality is distinctly lowered. This problem can be solved by using, for the removal of the product amide from the catalyst and the polymerization inhibitors and also the high-boiling by-products, an apparatus having gentle film evaporation as (5). Suitable apparatus known for this purpose includes falling-film, thin-layer and short-path evaporators.

The preparation of the alkylaminoacrylamides can optionally be followed by a purifying distillation plant which can also be operated under reduced pressure, for example at 500-0.1 mbar.

The process according to the invention is illustrated in detail by the example which follows without being restricted thereto.

EXAMPLE

Continuous Aminolysis to Aminoacrylamide

For the continuous preparation of N-dimethylaminopropylacrylamide, 200 kg/h of butyl acrylate/catalyst feed having a fraction of 2.0% by weight of isopropyl titanate 5.0% by weight of dioctyltin oxide of the distillation column (2) and 144 kg/h of N-dimethylaminopropylamine (DMAPA) were metered to the 1st reaction tank. In addition, the circulation return stream from the top of the low boiler distillation column flowed continuously to the 1st reaction tank via the distillation column (2) (400 kg/h with the composition of 70% by weight of reactant acrylate and also butyl alcohol, DMAPA and by-products). The molar butyl acrylate: DMAPA ratio in the reactor feed was 1.8:1. In addition, the vapours, freed of butanol in the distillation column (2), of the stirred tank flowed via the column bottom to the 1st reaction tank. Under these reaction conditions (pressure approx. 500 mbar), a reaction temperature of 138° C. was established in the 1st reaction tank. The reaction temperature in the 2nd and 3rd reaction tank was 143 and 155° C. respectively. The distillate draw of the distillation column (2) was 110 kg/h.

The effluent of the 1st reaction tank flowed into the 2nd reaction tank and the effluent of the 2nd reaction tank flowed into the 3rd reaction tank. At a residence time of approx. 150 min in total, the following fractions of the components were determined in the effluent of the 3rd reaction tank:

| butyl acrylate | 43% by weight |
| DMAPA | 4.86% by weight |
| amino amide | 35% by weight |

The vapours of the individual reaction tanks were fed continuously to the distillation column (2).

The effluent of the 3rd reaction tank flowed continuously to the thin-film evaporator of a low boiler column in which unconverted DMAPA, butyl acrylate and butanol were drawn off as distillate (400 kg/h) and fed back as circulation return stream to the distillation column (2). The bottom effluent of the thin-film evaporator of the low boiler column was 240 kg/h and had the composition: approx. 90% product amide, 0.1% DMAPA, a larger fraction of high-boiling components and traces of the reactants.

The invention claimed is:

1. A process for continuously preparing an alkylaminoacrylamide of formula (C)

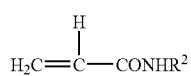 (C)

in which $R^2$ is a linear, branched, cyclic alkyl or aryl radical having 1 to 12 carbon atoms, said process comprising:
reacting a compound of formula (B)

 (B)

in which $R^2$ is as defined above with an alkyl acrylate of formula (A)

 (A)

in which $R^1$ is a linear or branched alkyl radical having 3 to 10 carbon atoms in the presence of an aminolysis catalyst or an aminolysis catalyst mixture and at least one polymerization inhibitor in an apparatus for continuous reaction,
wherein
before entry into the reaction apparatus, the compound of formula (B) is dewatered,
the reactants are fed continuously to a suitable reaction apparatus and the alcohol formed in the reaction or an alcohol/alkyl acrylate mixture is drawn off continuously with the aid of a distillation column, and
the reaction mixture is conducted continuously out of the reaction apparatus into a distillation column or an evaporator, in which distillation under reduced pressure draws off overhead volatile components (A), (B) and alcohol and a very small fraction of product amide (C) which are recycled into the reaction apparatus, and the product amides (C) are drawn off from the bottom of the column together with the catalyst and the polymerization inhibitors as well as high-boiling by-products; and the bottom stream from distillation column is fed continuously to a purifying distillation.

2. The process according to claim 1, wherein the vapour stream of evaporator is fed continuously to a further distillation column in which distillation under reduced pressure removes the highly pure product amide (C) overhead, while the catalyst and the polymerization inhibitors as well as high-boiling by-products are drawn off via the bottom with a small portion of product amide (C).

3. The process according to claim 1, wherein amine (B) is fed to the reaction apparatus for dewatering by means of the distillation column.

4. The process according to claim 1, wherein the molar ratio of alkyl acrylate to amine in the feed is between 1 and 2.

5. The process according to claim 1, wherein the catalyst used is a tetraalkyl titanate.

6. The process according to claim 1, wherein the catalyst is used in an amount of 0.1-10% by weight based on acrylate used.

7. The process according to claim 1, wherein the catalyst is used in an amount of 0.2-7% by weight based on acrylate used.

8. The process according to claim 1, wherein the catalyst mixture employed is a mixture of dioctyltin oxide and isopropyl titanate in a ratio of 2.5:1 (% by weight/% by weight).

9. The process according to claim 8, wherein the catalyst mixture is used in an amount of 0.1-10% by weight based on acrylate used.

10. The process according to claim 1, wherein the polymerization inhibitor used is either phenothiazine, tert-butylcatechol, hydroquinone monomethyl ether, hydroquinone or mixtures thereof, the amount of the inhibitor being between 100 and 5000 ppm based on the reaction mixture.

11. The process according to claim 1, wherein oxygen is used additionally as a polymerization inhibitor.

12. The process according to claim 1, wherein the amine used is dimethylaminopropylamine.

13. The process according to claim 1, wherein the pressure in the first distillation column is between 2 and 500 mbar.

14. The process according to claim 1, wherein the residence time in the reaction apparatus is between 0.5 and 3 hours.

15. The process according to claim 1, wherein the evaporator is a film evaporator.

16. The process according to claim 1, wherein said aminolysis catalyst is a transesterification catalyst.

17. The process according to claim 1, wherein the component (B) is dewatered distillatively using the distillation column, to remove the water present in the amine overhead.

18. The process according to claim 17, wherein the component (B) is introduced in the lower section of the distillation column, to prevent contamination of the low boiler discharge with the amine used.

19. The process according to claim 1, wherein the component (B) is dewatered by an upstream dewatering distillation column or by treating with a dewatering agent or by a membrane separation process.

20. The process according to claim 1, wherein the dewatering of component (B) prevents the hydrolysis of the catalyst.

* * * * *